United States Patent [19]

Fleischle

[11] Plant 4,527

[45] Apr. 29, 1980

[54] DISTINCT VARIETY OF STREPTOCARPUS NAMED VELMA

[75] Inventor: Gerhard Fleischle, Vaihingen, Fed. Rep. of Germany

[73] Assignee: Oglevee Associates, Inc., Connellsville, Pa.

[21] Appl. No.: 958,832

[22] Filed: Nov. 8, 1978

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Webb, Burden, Robinson & Webb

[57] ABSTRACT

A new variety of streptocarpus plant is characterized by its amethyst flower having a yellow throat. It has large flowers, long permanence and is generally nonfertile.

1 Drawing Figure

BACKGROUND OF THE NEW PLANT

The present invention comprises a new and distinct cultivar of *streptocarpus* × *hybridus* known by the varietal name of Velma, formerly named Neptune Rose. The cultivar is an irradiated sport of Neptune Blue.

Velma is virtually identical to Neptune Blue except for the color of the flower.

The new cultivar was discovered in 1977 in Vaihingen, Federal Republic of Germany; was first asexually reproduced by cuttings in Vaihingen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of eight weeks from a plantlet (a well rooted young plant in a five centimeter pot) to a flowering plant in a ten centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on eight week plants blossomed under natural light in a greenhouse and color readings were taken indoors under 100 foot candles of cool white fluorescent light. Color references are primarily to the R.H.S. color chart of the Royal Horticultural Society of London. Some color reference is to Exotica III and such reference is duly noted.

Botanical classification: Gesneriaceae (Family); *Streptocarpus* × *hybridus* (Genus × species).

FLOWER:

*Fully expanded.*—Six centimeters.

*Borne.*—In clusters of one to six flowers per flower stalk above the foliage. Flower stalks arise from mid-rib of each leaf.

*Stems.*—Single, long and pubescent.

*Form.*—Funnel formed in an umbel.

*Permanence.*—Long lasting 21 to 25 days.

*Color.*—Front of petals — Fan 2 Purple Group 78-A. Throat — Fan 1 Yellow Green Group 154-B with some striping, Purple Violet Group 80-A, extending into the center of the petals. Base of petals — Fan 2 Red Purple Group 69-D. Reverse of petals — Fan 2 Purple Group 78-B. Tonality from a distance — Purple to amethyst (Exotica III). Discoloration — Insignificant.

Petals:

*Texture.*—Velvet.

*Appearance.*—Individually lobed with ruffled to serrated margin.

*Arrangement.*—Regularly united into an elliptical form.

*Persistance.*—Lives for 21 to 25 days and remains on plant in dry form until picked.

*Fragrance.*—None.

Reproductive organs:

*Anthers.*—Two per flower and interconnected.

*Filament.*—Two and one-half centimeters initiating from the base of petal and extending to the anther.

*Pollen.*—Generally nonfertile.

*Style.*—Extends from tip of ovary one centimeter and terminates in a flattened stigma.

*Ovaries.*—Long and narrow, one and one-half millimeters in diameter and one and one-half centimeters long.

Plant:

*Form.*—Leaves rosulete from a crown at the soil line.

*Growth.*—A spreading, free flowing habit with leaf bases being acute.

*Height from soil line.*—15 to 20 centimeters.

*Spread.*—35 to 40 centimeters.

Foliage:

*Top side.*—Fan 3 Green Group 137-B.

*Size.*—Approximately 20 centimeters in length and 5 to 10 centimeters in width at widest point.

*Quantity.*—10 to 15 leaves.

*Shape.*—Oblanceolete.

*Ribs and veins.*—Pinnate.

*Rib and vein color.*—Fan 3 Green Group 138-B.

*Margin.*—Crenate serrations.

*Underside.*—Fan 4 Greyed Green Group 193-A.

*Stipules.*—None.

I claim:

1. A new and distinct variety of streptocarpus substantially as herein shown and described.

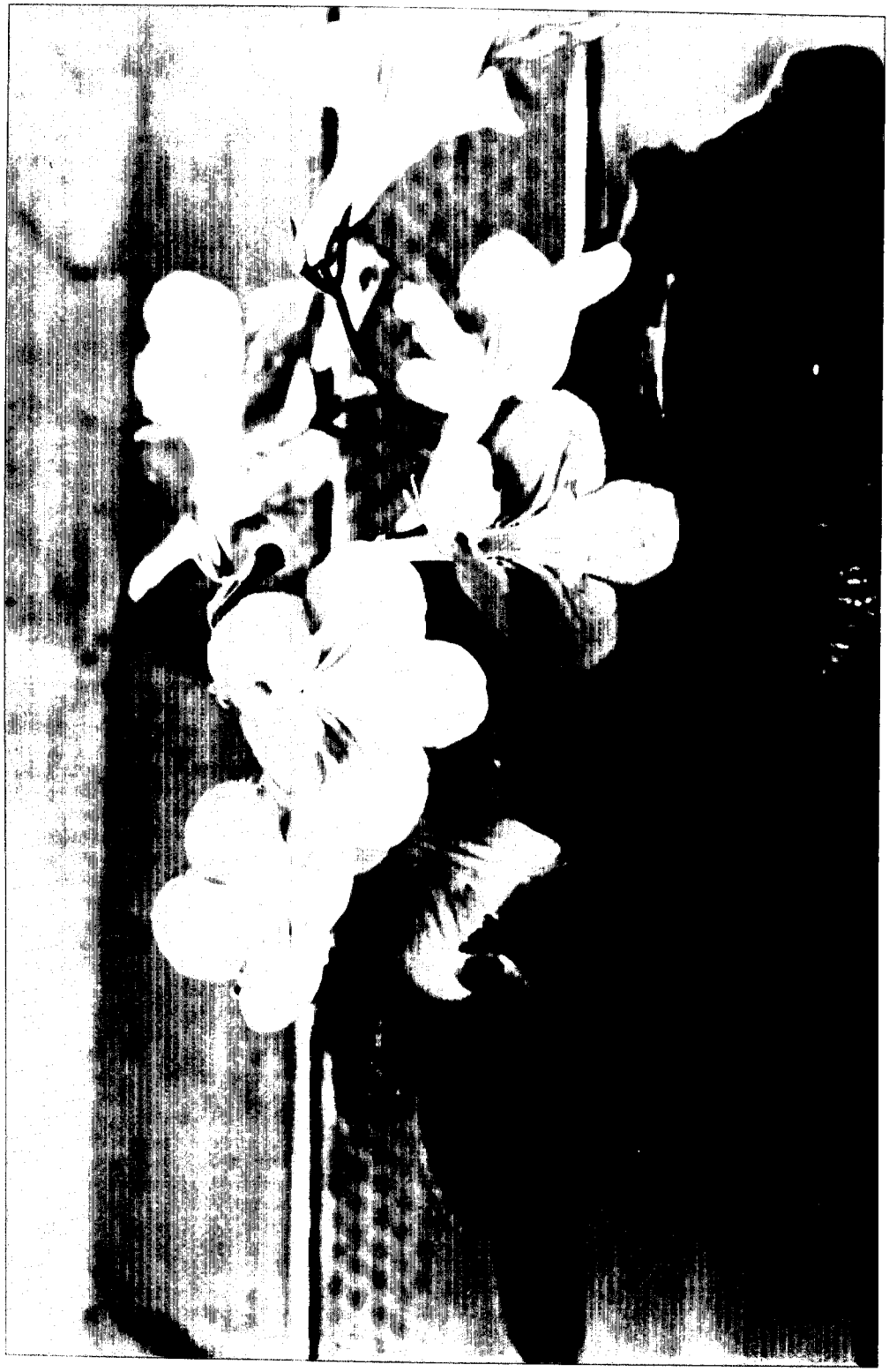

* * * * *